United States Patent
Suwito

(10) Patent No.: US 11,612,733 B2
(45) Date of Patent: Mar. 28, 2023

(54) SCREW CONTROL MEDICAL FLUID FLOW MANIFOLDS

(71) Applicant: CareFusion 303, Inc., San Diego, CA (US)

(72) Inventor: Wantjinarjo Suwito, West Linn, OR (US)

(73) Assignee: CAREFUSION 303, INC., San Diego, CA (US)

( * ) Notice: Subject to any disclaimer, the term of this patent is extended or adjusted under 35 U.S.C. 154(b) by 352 days.

(21) Appl. No.: 16/857,085

(22) Filed: Apr. 23, 2020

(65) Prior Publication Data

US 2021/0330955 A1 Oct. 28, 2021

(51) Int. Cl.
*A61M 39/22* (2006.01)
*A61M 5/14* (2006.01)
(Continued)

(52) U.S. Cl.
CPC .......... *A61M 39/22* (2013.01); *A61M 5/1408* (2013.01); *A61M 5/16881* (2013.01);
(Continued)

(58) Field of Classification Search
CPC .............. A61M 5/1407; A61M 5/1408; A61M 5/1409; A61M 5/16881; A61M 39/10; A61M 39/22; A61M 39/223; A61M 39/225; A61M 2039/009; A61M 2039/1027; A61M 2039/226; A61M 2039/229; A61M 2039/267; A61M 2039/0009; A61M 2039/0018; F16K 11/04; F16K 31/50; F16K 31/504; F16K 37/0008; F16K 37/0016;
(Continued)

(56) References Cited

U.S. PATENT DOCUMENTS 316,675 A * 4/1885 Vance ..................... F16K 41/02
251/284
1,354,582 A * 10/1920 Shimp ................. F16K 27/0263
122/DIG. 15
(Continued)

FOREIGN PATENT DOCUMENTS

FR         2358601 A1    2/1978
WO    WO-2015154303 A1   10/2015

OTHER PUBLICATIONS

International Search Report and Written Opinion for Application No. PCT/US2021/028703, dated Aug. 13, 2021, 17 pages.

*Primary Examiner* — Kenneth Rinehart
*Assistant Examiner* — Jonathan J Waddy
(74) *Attorney, Agent, or Firm* — Morgan, Lewis & Bockius LLP

(57) ABSTRACT

Fluid flow manifold assemblies for use in fluid flow sets are provided. The fluid flow manifold assembly includes a body having a main fluid channel and a reinforcing plate, the main fluid channel having a fluid inlet, a fluid outlet and a drug port. A flow control assembly is disposed opposite the main fluid channel from the drug port. The flow control assembly is configured to shut off fluid flow through the drug port into the main fluid channel with a plunger of the flow control assembly in a closed position and to allow incremental levels of fluid flow through the drug port into the main fluid channel by variably retracting the plunger based on rotation of a knob of the flow control assembly.

18 Claims, 6 Drawing Sheets

(51) Int. Cl.
*A61M 5/168* (2006.01)
*A61M 39/00* (2006.01)
*F16K 37/00* (2006.01)

(52) U.S. Cl.
CPC .............. *A61M 2039/0009* (2013.01); *A61M 2039/226* (2013.01); *F16K 37/00* (2013.01); *Y10T 137/8225* (2015.04); *Y10T 137/87676* (2015.04)

(58) Field of Classification Search
CPC ...... F16K 11/20; F16K 37/00; F16K 37/0058; Y10T 137/8158; Y10T 137/8225; Y10T 137/87676; Y10T 137/87684
USPC .................. 137/553; 251/264, 284, 286, 288
See application file for complete search history.

(56) References Cited

U.S. PATENT DOCUMENTS

| | | | | |
|---|---|---|---|---|
| 2,206,688 A * | 7/1940 | Bloomheart | ......... | A61M 16/18 137/553 |
| 2,908,476 A * | 10/1959 | Hidding | ............. | A61M 39/284 D24/129 |
| 3,057,596 A * | 10/1962 | Tobin | ...................... | F16K 41/00 251/285 |
| 3,198,206 A * | 8/1965 | O'Brien | ................ | F16L 41/065 137/315.42 |
| 3,253,612 A * | 5/1966 | Curatolapaulc | ......... | F16K 1/523 137/553 |
| 3,583,441 A * | 6/1971 | Grant | ..................... | F16K 11/04 137/625.48 |
| 3,603,347 A * | 9/1971 | Paolini | .................. | F16K 11/065 251/263 |
| 3,739,804 A * | 6/1973 | Dubreuil | ................ | F16K 11/04 137/269 |
| 3,797,524 A * | 3/1974 | Sanelli | .................... | F16K 11/20 251/121 |
| 4,550,748 A * | 11/1985 | Nunez | ................. | A61M 39/225 604/250 |
| 4,624,662 A * | 11/1986 | Le | ....................... | A61M 39/225 251/117 |
| 4,915,688 A * | 4/1990 | Bischof | .................. | A61J 3/002 604/83 |
| 5,618,268 A * | 4/1997 | Raines | .................. | A61M 39/26 604/82 |
| 6,083,205 A | 7/2000 | Bourne et al. | | |
| 6,099,511 A * | 8/2000 | Devos | ................. | A61M 5/1408 604/82 |
| 6,626,884 B1* | 9/2003 | Dillon | ................... | A61B 5/155 604/323 |
| 2004/0221904 A1* | 11/2004 | Usher | ................... | A61M 39/24 137/837 |
| 2004/0249235 A1* | 12/2004 | Connell | ................. | A61J 1/20 588/1 |
| 2007/0232989 A1 | 10/2007 | Kitani et al. | | |
| 2010/0168664 A1* | 7/2010 | Zinger | .................. | A61J 1/2096 604/89 |
| 2011/0085936 A1 | 4/2011 | Haytman et al. | | |
| 2013/0008546 A1* | 1/2013 | Haimi | .............. | A61M 5/16813 138/89 |
| 2014/0107480 A1* | 4/2014 | Spohn | .................. | A61M 5/158 600/432 |
| 2016/0279404 A1* | 9/2016 | Nelson | .................. | A61M 39/10 |
| 2017/0113031 A1* | 4/2017 | Ueda | ................. | A61M 39/223 |

* cited by examiner

SCREW CONTROL MEDICAL FLUID FLOW MANIFOLDS

CROSS-REFERENCES TO RELATED APPLICATIONS

N/A

BACKGROUND

Medical fluid flow manifolds are used in the medical field for controlling fluid flow to a patient, such as for anesthesia fluid flow from a pump set. Typical fluid flow manifolds use a stopcock mechanism that a user can turn to change the fluid flow through the corresponding manifold. A stopcock mechanism may be easy to turn but is not necessarily intuitive to use, such as which direction will result in restricting or opening the fluid flow. Also, stopcock mechanisms are prone to have dead spaces that prevent a clean flush of one fluid (e.g., an anesthesia drug) before introducing another fluid (e.g., a different anesthesia drug) through the same manifold. It is desirable to provide medical fluid flow manifolds having safe, consistent fluid flow control that are intuitive to use and do not have dead spaces, thus improving safety and reducing risks.

SUMMARY

The present disclosure provides medical fluid flow manifolds having screw control mechanisms.

In one or more embodiments, a fluid flow manifold assembly is provided. The fluid flow manifold assembly includes a body having a main fluid channel and a reinforcing plate. The fluid flow manifold assembly also includes a fluid inlet disposed on a first end of the main fluid channel, a fluid outlet disposed on a second end of the main fluid channel and a drug port coupled to the main fluid channel and disposed at an angle to the main fluid channel. The fluid flow manifold assembly further includes a flow control assembly coupled to the main fluid channel and opposing the drug port. The flow control assembly includes a plunger, a seal member, a cap thread and a knob. The flow control assembly is configured to shut off fluid flow through the drug port with the plunger disposed in a first position, to allow a maximum fluid flow through the drug port with the plunger disposed in a second position, and to allow incremental levels of fluid flow through the drug port with the plunger disposed in varying positions between the first and second positions, wherein the plunger position is based on rotation of the knob in one of a clockwise and a counterclockwise direction.

In one or more aspects, the drug port is disposed orthogonally to the main fluid channel and the flow control assembly is disposed axially to the drug port. In one or more aspects, an inlet connector is coupled to the fluid inlet. In one or more aspects, the inlet connector is a female Luer connector. In one or more aspects, an outlet connector is coupled to the fluid outlet. In one or more aspects, the outlet connector is a male Luer connector. In one or more aspects, a port connector is coupled to the drug port. In one or more aspects, the port connector is a female Luer connector. In one or more aspects, a cavity is disposed in the reinforcement plate, wherein the knob is disposed within the cavity. In one or more aspects, the cavity has a stop surface configured to prevent the knob from being rotated further in a counterclockwise direction. In one or more aspects, an indicator element is disposed on the reinforcement plate. In one or more aspects, the indicator element is one of printed on the reinforcement plate, etched onto the reinforcement plate and formed by a material of the reinforcement plate. In one or more aspects, the fluid flow manifold assembly is configured to prevent a dead space when the plunger is disposed in any position between and including the first position and the second position. In one or more aspects, the fluid flow manifold assembly is configured to allow fluid flow through the main fluid channel from the fluid inlet with any position of the plunger between and including the first position and the second position.

In one or more embodiments, a fluid flow set is provided. The fluid flow set includes a fluid inlet tube, a fluid outlet tube, a drug delivery tube and a fluid flow manifold assembly. The fluid flow manifold assembly includes a body having a main fluid channel and a reinforcing plate. The fluid flow manifold assembly also includes an inlet connector disposed on a first end of the main fluid channel and coupled to the fluid inlet tube, an outlet connector disposed on a second end of the main fluid channel and coupled to the fluid outlet tube, and a port connector coupled to the main fluid channel and coupled to the drug delivery tube. The fluid flow manifold assembly further includes a flow control assembly coupled to the main fluid channel opposing the port connector, the flow control assembly comprising a plunger, a seal member, a cap thread and a knob. The flow control assembly is configured to shut off fluid flow into the main fluid channel from the drug delivery tube with the plunger disposed in a first position, to allow a maximum fluid flow into the main fluid channel from the drug delivery tube with the plunger disposed in a second position, and to allow incremental levels of fluid flow into the main fluid channel from the drug delivery tube with the plunger disposed in varying positions between the first and second positions. The plunger position is based on rotation of the knob in one of a clockwise and a counterclockwise direction.

In one or more aspects, the fluid flow manifold assembly is an anesthesia manifold. In one or more aspects, the fluid flow manifold assembly comprises three drug ports, each drug port coupled to a separate port connector and each separate port connector coupled to a separate drug delivery tube. In one or more aspects, the fluid flow manifold assembly further includes a cavity disposed in the reinforcement plate, the cavity having a stop surface configured to prevent the knob from being loosened past a defined point. In one or more aspects, the fluid flow manifold assembly is configured to prevent a dead space when the plunger is disposed in any position between and including the first position and the second position. In one or more aspects, the fluid flow manifold assembly is configured to allow fluid flow through the main fluid channel from the fluid inlet with any position of the plunger between and including the first position and the second position.

Additional features and advantages of the disclosure will be set forth in the description below and, in part, will be apparent from the description or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Fluid flow sets (e.g., IV anesthesia sets) may be formed from any combination of fluid flow components and tubing. Typically, the fluid flow components and tubing are fixedly connected together to form a disposable fluid flow set that is used once and then discarded. The fluid flow components and tubing may be formed from any suitable material (e.g., plastic, silicone, rubber).

Figure 1:
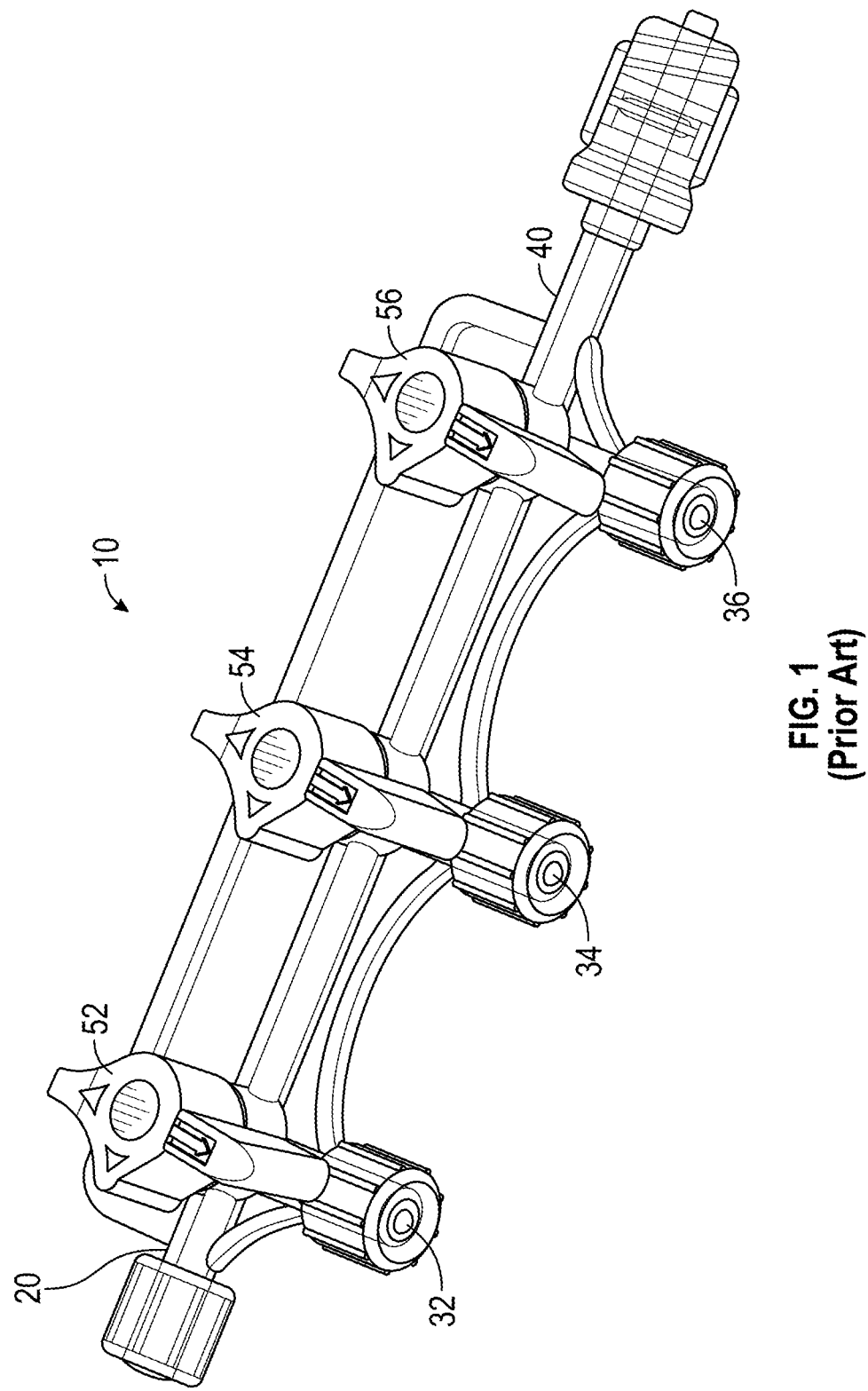
FIG. 1 is a perspective view of a typical fluid flow manifold with stopcocks.
Figure 2:
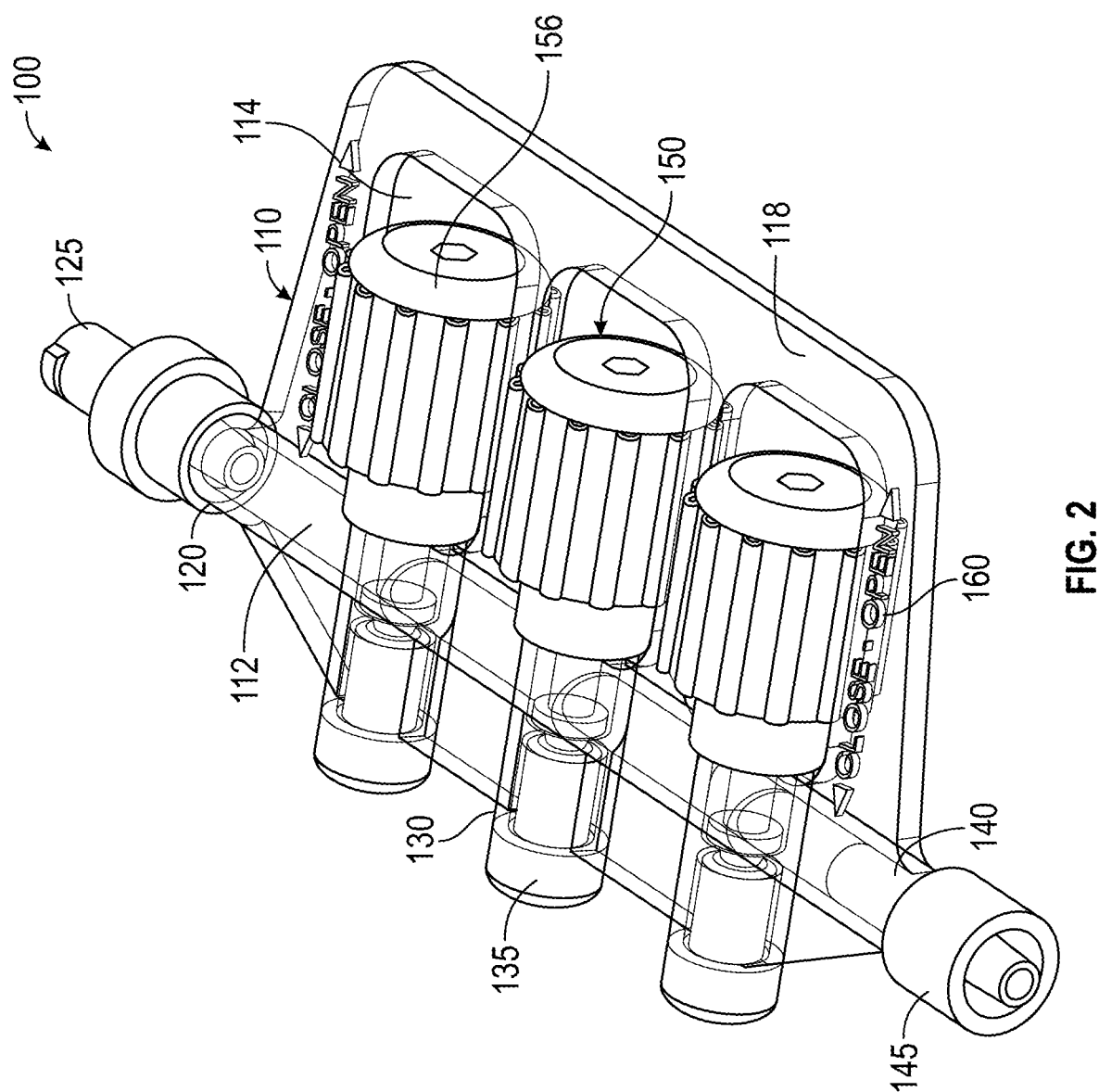
FIG. 2 is a perspective view of an example medical fluid flow manifold, according to some aspects of the disclosure.

A typical fluid flow manifold 10 is shown in FIG. 1 as a three port anesthesia manifold. The fluid flow manifold 10 includes a saline inlet port 20, three drug inlet ports 32, 34, 36 and an outlet port 40. Fluid flow from the drug inlet ports 32, 34, 36 are controlled by corresponding stopcocks 52, 54, 56. However, typical stopcocks can be confusing as to what position the stopcock needs to be turned to in order to stop the fluid flow or in order to redirect fluid to which channel. This is especially true for 3-way stopcocks such as stopcocks 52, 54, 56.

For example, a quarter turn of stopcock 52, 54, 56 may change the fluid flow from the corresponding drug inlet port 32, 34, 36 from open to closed, while another quarter turn of stopcock 52, 54, 56 may open or close fluid flow from upstream (e.g., the saline inlet port 20). However, an absence of clear visual cues and a non-intuitive function of the stopcock 52, 54, 56 may lead to errors in delivering the right quantities and/or types of medications. Further, stopcocks 52, 54, 56 may have left over medication remaining in the area of the stopcock 52, 54, 56 after being turned to a closed position (e.g., dead space). Thus, when a new medication is introduced to that inlet port 32, 34, 36, the remaining portion of the previous medication in the dead space is mixed with the new medication to be delivered.

FIGS. 2-7 illustrate a fluid flow manifold assembly shown as fluid flow manifold 100, according to some aspects of the disclosure. The fluid flow manifold 100 is shown here as a 3-port fluid manifold having a body 110 with a main fluid channel 112 and three cavities 114. The body 110 has a fluid inlet 120 at one end of the main fluid channel 112 and a fluid outlet 140 at the other end of the main fluid channel 112. The body 110 also includes three drug ports 130 that provide for introducing drugs and/or medications into the main fluid channel 112. Here, the drug ports 130 are orthogonal to the main fluid channel 112. In some aspects of the disclosure, the drug ports 130 may be disposed at any desired angle respective to the main fluid channel 112. The body 110 also includes a reinforcement plate 118 that strengthens the fluid flow manifold 100 structure. The reinforcement plate 118 also provides an easy and intuitive surface for gripping the fluid flow manifold 100.

Port connectors 135 (e.g., female Luer connector) are coupled to the drug ports 130, an inlet connector 125 (e.g., female Luer connector) is coupled to the fluid inlet 120 and an outlet connector 145 (e.g., male Luer connector) is coupled to the fluid outlet 140. The fluid flow manifold 100 also includes flow control assemblies 150 coupled to the main fluid channel 112 and opposing corresponding drug ports 130. Each flow control assembly 150 includes a plunger 152, a seal member 154, a knob 156 and a cap thread 158, where the knob 156 is disposed within a cavity 114. The seal member 154 sealingly engages with the cap thread 158 and the plunger 152 slidingly engages with the seal member 154, thus providing a barrier to fluid and preventing fluid from leaking out of the flow control device 150.

Figure 4:
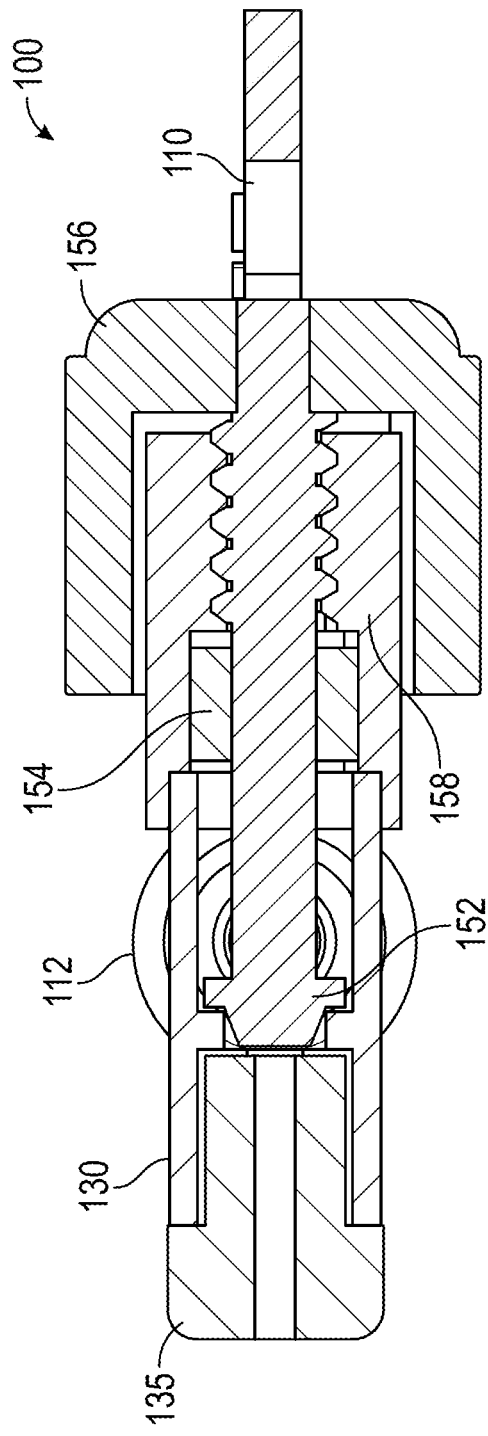
FIG. 4 is a cross-sectional side view of the medical fluid flow manifold of FIG. 2 with a flow control mechanism in a closed position, according to some aspects of the disclosure.

The knob 156 is configured to turn clockwise so that the cap thread 158 moves the plunger 152 towards the drug port 130 to engage with the port connector 135 to close off or block the fluid flow coming in through the drug port 130 (see FIG. 4). The knob 156 is also configured to turn counterclockwise so that the cap thread 158 moves the plunger 152 away from the drug port 130 to open a fluid flow coming in through the port connector 135 (see FIG. 5). As shown in FIG. 4, when the drug port 130 is closed (e.g., sealed by the plunger 152), fluid can still freely flow through the main fluid channel 112 by flowing over and under (e.g., around) the plunger 152 disposed across the main fluid channel 112. For example, if all three flow control assemblies 150 are fully closed, fluid (e.g., saline) coming downstream from the fluid inlet 120 can still flow through the main fluid channel 112 and out the fluid outlet 140. Also, when the flow control assembly 150 is in the closed position, there is no dead space created by the plunger 152 and any fluid from the drug port 130 that remains in the main fluid channel 112 after the drug port 130 is closed (e.g., sealed by the plunger 152) is flushed by fluid coming downstream from the fluid inlet 120.

Figure 3:
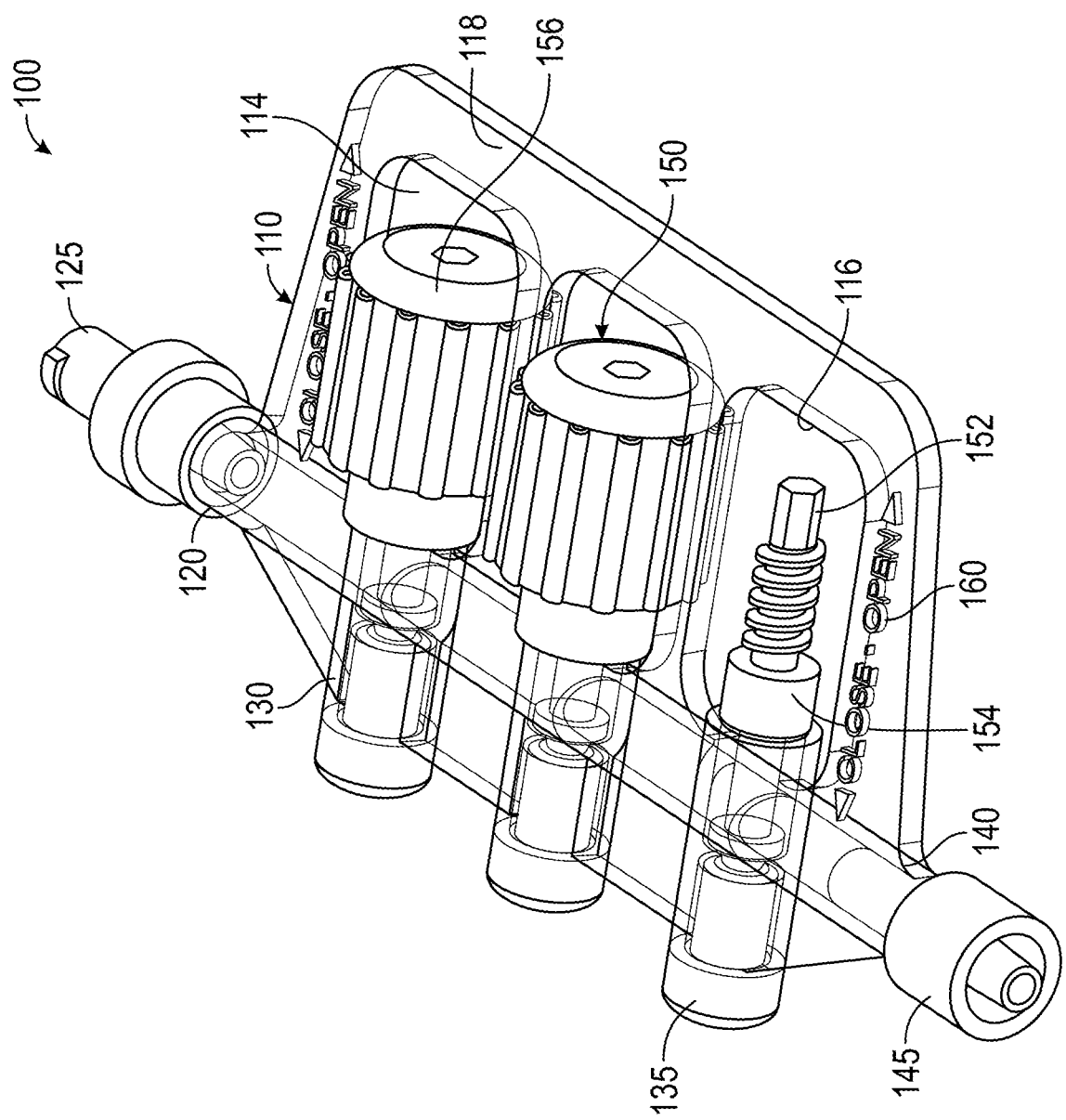
FIG. 3 is a perspective view of the medical fluid flow manifold of FIG. 2 with a knob removed, according to some aspects of the disclosure.
Figure 5:
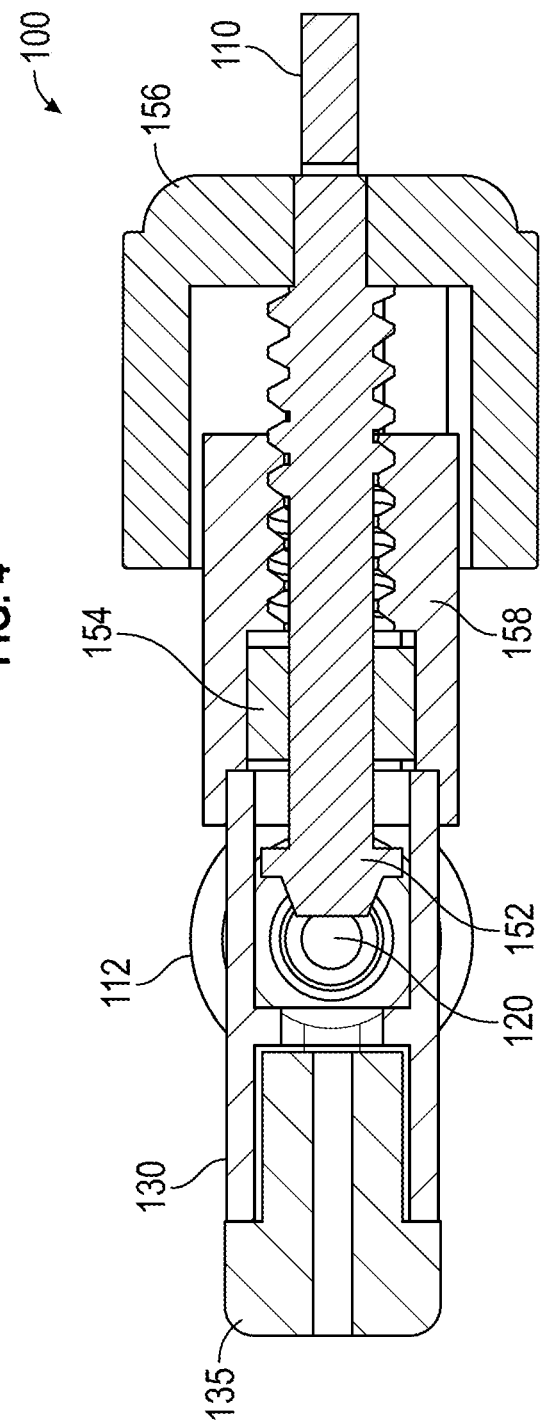
FIG. 5 is a cross-sectional side view of the medical fluid flow manifold of FIG. 2 with a flow control mechanism in an open position, according to some aspects of the disclosure.
Figure 6:
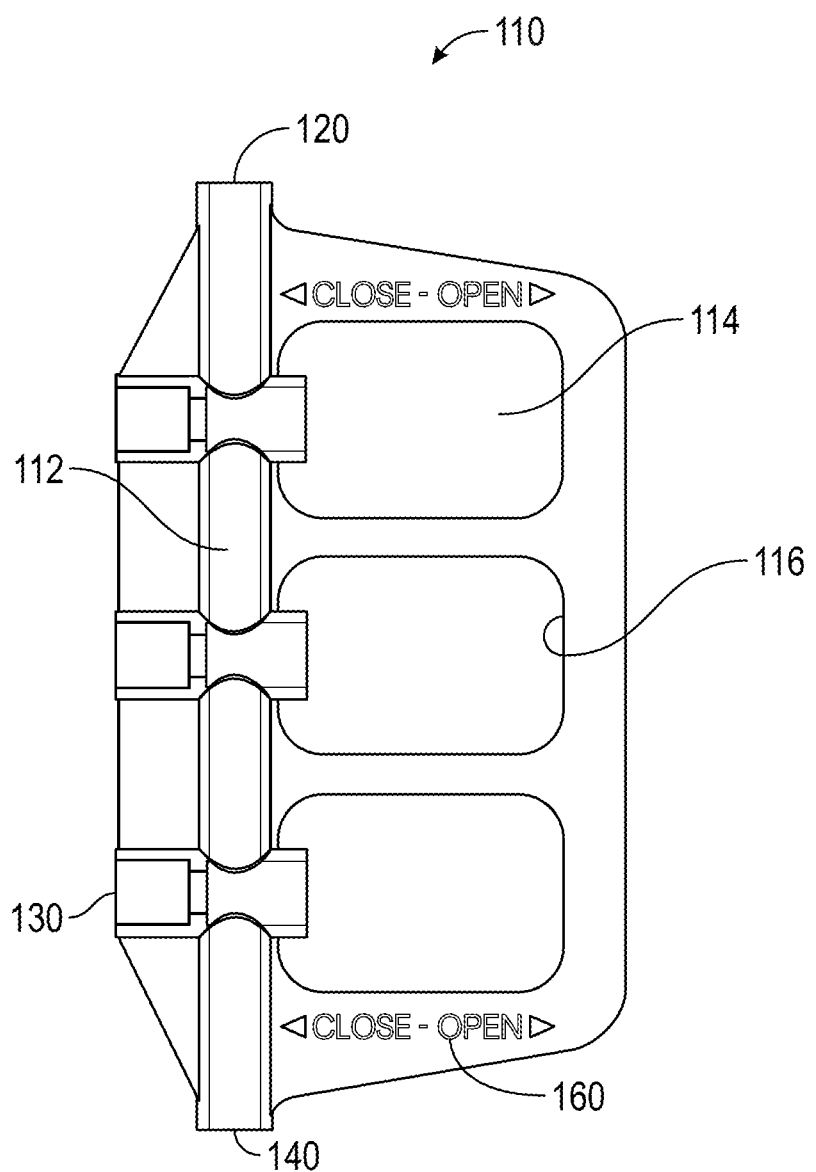
FIG. 6 is a top view of the body of the medical fluid flow manifold of FIG. 2, according to some aspects of the disclosure.
Figure 7:
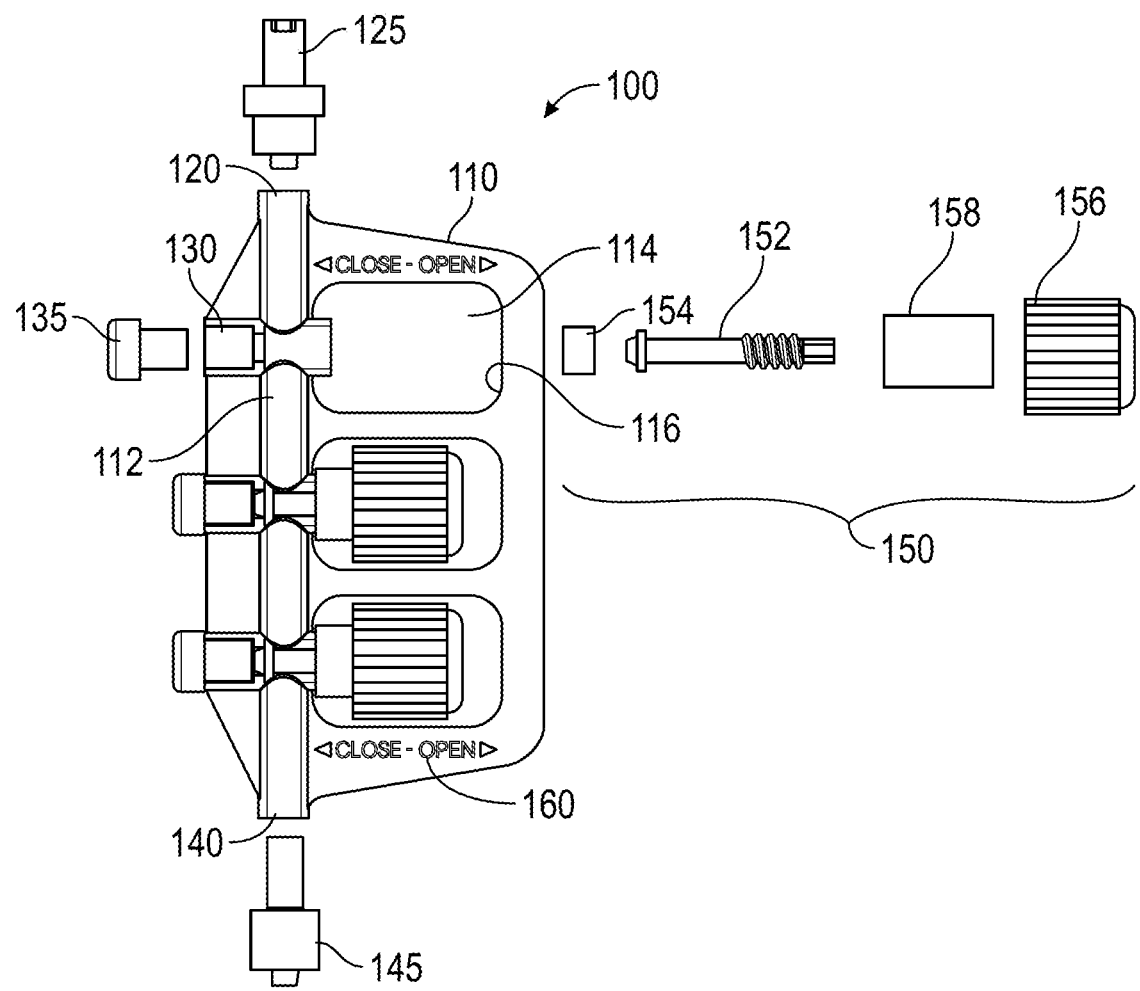
FIG. 7 is an exploded top view of the medical fluid flow manifold of FIG. 2, according to some aspects of the disclosure.

As shown in FIG. 3, the reinforcement plate 118 has a stop surface 116 of the cavity 114 that may be configured as a hard stop for the knob 156, thereby preventing the knob 156 from being turned any further in the counterclockwise direction. For example, the stop surface 116 may prevent the knob 156 from being dislodged from the fluid flow manifold 100 or from fully unscrewing off of the plunger 152. This fully open position may be configured to extract the plunger 152 a defined distance out of the main fluid channel 112. For example, the plunger 152 may be extracted most of the way out of the main fluid channel 112 as shown in FIG. 5. As another example, the fully open position may be configured to extract the plunger 152 completely out of the main fluid channel 112. The extracted position of the plunger 152 may be determined by the size of the cavity 114 and in turn the position of the stop surface 116.

The body 110 may further include one or more indicator elements 160 to provide a visual indication for operation of the flow control assemblies 150. In some aspects, the indicator element 160 may be printed or etched onto the body 110, or formed/embedded within the material of the body 110. Thus, in addition to the intuitive clockwise/counterclockwise rotation of the knob 156 to open and close the flow control assembly 150, the indicator element 160 is configured to further indicate the proper turning direction of the knob 156 to open or close the drug port 130.

The body 110 may be formed of an elastic material, such as plastic or silicone rubber, for example. The plunger 152 and the outlet connector 145 may be formed of a metallic material, such as stainless steel or titanium, for example. The inlet connector 125, the port connector 135, the cap thread 158 and the knob 156 may be formed of generally inelastic material, such as hard plastic or silicone, for example. All of the above-described materials may be biocompatible materials.

The drug port 130 may be sized and shaped to receive any type of port connector 135, such as any type of needleless connector. For example, the drug port 130 may be sized and shaped to conform to dimensions of standard tubing used in IV sets. Similarly, the fluid inlet 120 and the fluid outlet 140 may be sized and shaped to receive any type of inlet and outlet connector, respectively (e.g., female Luer connector, male Luer connector). For example, the fluid inlet 120 and fluid outlet 140 may be sized and shaped to conform to dimensions of standard tubing used in IV sets. Accordingly, each of the fluid inlet 120, the drug port 130 and the fluid outlet 140 may be configured to couple with standard IV set components.

The fluid flow manifold 100 may be configured for any type of fluid flow application. For example, the fluid flow manifold 100 may be configured as an anesthesia manifold for delivery of anesthesia drugs and fluids. As another example, the fluid flow manifold 100 may be configured for use in an IV infusion set, such as gravity IV sets and pump infusion IV sets. The fluid flow manifold 100 is illustrated with three drug ports 130, but may be configured with any number of drug ports 130 from one on up.

The screw mechanism of the flow control assembly 150 provides for incremental flow control from the drug port 130. For example, as the knob 156 is unscrewed and the plunger is correspondingly retracted from the port connector 135, the amount or rate of fluid flow from the drug port 130 incrementally increases as the plunger 152 is further retracted until the knob 156 reaches the stop surface 116 and the fluid flow from the drug port 130 is maximized. By contrast, a stopcock mechanism is typically an on/off control where the fluid flow is fully open or shut off, with no incremental gradations in between.

The fluid flow manifold 100 may be manufactured as a complete assembly, including any or all of the inlet connector 125, the port connector(s) 135 and the outlet connector 145, any of which may further be capped with a protective cap that may be removed for use. Similarly, any or all of the inlet port 120, the drug ports 130 and the outlet port 140 may be capped with a protective cap that may be removed for insertion of the corresponding inlet connector 125, the port connector 135 and the outlet connector 145. Thus, each fluid entry or exit point of the main fluid channel 112 may be protected from contamination up to and during its use.

The fluid flow manifold 100 is configured to be intuitive to use, to be safe to use with no dead spaces and to have granular/incremental flow control for each drug port 130. The fluid flow manifold 100 may be configured for use with liquid fluid flow, according to some aspects of the disclosure. The fluid flow manifold 100 may be configured for use with gaseous fluid flow, according to some aspects of the disclosure.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. A fluid flow manifold assembly, comprising:
    a body having a main fluid channel and an integral reinforcing plate extending outward from the main fluid channel, the reinforcing plate having a surface for gripping the fluid flow manifold assembly;
    a fluid inlet disposed on a first end of the main fluid channel;
    an inlet connector coupled to the fluid inlet, the inlet connector comprising a female Luer connector;
    a fluid outlet disposed on a second end of the main fluid channel;
    a drug port coupled to the main fluid channel and disposed at an angle to the main fluid channel; and
    a flow control assembly coupled to the main fluid channel and opposing the drug port, the flow control assembly comprising:
        a plunger;
        a seal member disposed outside of the main fluid channel, the plunger slidably engaged with the seal member;
        a cap thread disposed outside of the main fluid channel; and
        a knob disposed outside of the main fluid channel,
    wherein the flow control assembly is configured to shut off fluid flow through the drug port with the plunger disposed in a first position, to allow a maximum fluid flow through the drug port with the plunger disposed in a second position, and to allow incremental levels of fluid flow through the drug port with the plunger disposed in varying positions between the first and second positions, wherein the plunger position is based on rotation of the knob in one of a clockwise and a counterclockwise direction, wherein the plunger extends across the entire main fluid channel when the plunger is in the first position, and wherein an end portion of the plunger is disposed just within the main fluid channel when the plunger is in the second position.

2. The fluid flow manifold assembly of claim 1, wherein the drug port is disposed orthogonally to the main fluid channel and the flow control assembly is disposed axially to the drug port.

3. The fluid flow manifold assembly of claim 1, further comprising an outlet connector coupled to the fluid outlet.

4. The fluid flow manifold assembly of claim 3, wherein the outlet connector is a male Luer connector.

5. The fluid flow manifold assembly of claim 1, further comprising a port connector coupled to the drug port.

6. The fluid flow manifold assembly of claim 5, wherein the port connector is a female Luer connector.

7. The fluid flow manifold assembly of claim 1, further comprising a cavity disposed in the reinforcement plate, wherein the knob is disposed within the cavity.

8. The fluid flow manifold assembly of claim 7, wherein the cavity has a stop surface configured to prevent the knob from being rotated further in a counterclockwise direction.

9. The fluid flow manifold assembly of claim 1, further comprising an indicator element disposed on the reinforcement plate.

10. The fluid flow manifold assembly of claim 9, wherein the indicator element is one of printed on the reinforcement plate, etched onto the reinforcement plate and formed by a material of the reinforcement plate.

11. The fluid flow manifold assembly of claim 1, wherein the fluid flow manifold assembly is configured to prevent a dead space when the plunger is disposed in any position between and including the first position and the second position.

12. The fluid flow manifold assembly of claim 1, wherein the fluid flow manifold assembly is configured to allow fluid flow through the main fluid channel from the fluid inlet with any position of the plunger between and including the first position and the second position.

13. A fluid flow manifold assembly, comprising:
a body having a main fluid channel and an integral reinforcing plate extending outward from the main fluid channel, the reinforcing plate having a surface for gripping the fluid flow manifold assembly;
a fluid inlet disposed on a first end of the main fluid channel;
a fluid outlet disposed on a second end of the main fluid channel;
a drug port coupled to the main fluid channel and disposed at an angle to the main fluid channel;
one of an outlet connector comprising a male Luer connector coupled to the fluid outlet and a port connector comprising a female Luer connector coupled to the drug port; and
a flow control assembly coupled to the main fluid channel and opposing the drug port, the flow control assembly comprising:
a plunger;
a seal member disposed outside of the main fluid channel, the plunger slidably engaged with the seal member;
a cap thread disposed outside of the main fluid channel; and
a knob disposed outside of the main fluid channel,
wherein the flow control assembly is configured to shut off fluid flow through the drug port with the plunger disposed in a first position, to allow a maximum fluid flow through the drug port with the plunger disposed in a second position, and to allow incremental levels of fluid flow through the drug port with the plunger disposed in varying positions between the first and second positions, wherein the plunger position is based on rotation of the knob in one of a clockwise and a counterclockwise direction, wherein the plunger extends across the entire main fluid channel when the plunger is in the first position, and wherein an end portion of the plunger is disposed just within the main fluid channel when the plunger is in the second position.

14. A fluid flow set, comprising:
a fluid inlet tube;
a fluid outlet tube;
a drug delivery tube; and
a fluid flow manifold assembly, the fluid flow manifold assembly comprising:
a body having a main fluid channel and an integral reinforcing plate extending outward from the main fluid channel;
an inlet connector disposed on a first end of the main fluid channel and coupled to the fluid inlet tube;
an outlet connector disposed on a second end of the main fluid channel and coupled to the fluid outlet tube;
a port connector coupled to the main fluid channel and coupled to the drug delivery tube; and
a flow control assembly coupled to the main fluid channel opposing the port connector, the flow control assembly comprising a plunger, a seal member disposed outside of the main fluid channel, the plunger slidably engaged with the seal member, a cap thread disposed outside of the main fluid channel and a knob disposed outside of the main fluid channel,
wherein the flow control assembly is configured to shut off fluid flow into the main fluid channel from the drug delivery tube with the plunger disposed in a first position, to allow a maximum fluid flow into the main fluid channel from the drug delivery tube with the plunger disposed in a second position, and to allow incremental levels of fluid flow into the main fluid channel from the drug delivery tube with the plunger disposed in varying positions between the first and second positions,
wherein the plunger position is based on rotation of the knob in one of a clockwise and a counterclockwise direction,
wherein the plunger extends across the entire main fluid channel when the plunger is in the first position,
wherein the plunger is disposed completely outside the main fluid channel when the plunger is in the second position, and
wherein the fluid flow manifold assembly comprises three drug ports, each drug port coupled to a separate port connector and each separate port connector coupled to a separate drug delivery tube.

15. The fluid flow set of claim 14, wherein the fluid flow manifold assembly is an anesthesia manifold.

16. The fluid flow set of claim 14, the fluid flow manifold assembly further comprising a cavity disposed in the reinforcement plate, the cavity having a stop surface configured to prevent the knob from being loosened past a defined point.

17. The fluid flow set of claim 14, wherein the fluid flow manifold assembly is configured to prevent a dead space when the plunger is disposed in any position between and including the first position and the second position.

18. The fluid flow set of claim 14, wherein the fluid flow manifold assembly is configured to allow fluid flow through the main fluid channel from the fluid inlet with any position of the plunger between and including the first position and the second position.

\* \* \* \* \*